(12) United States Patent
Chandler et al.

(10) Patent No.: US 7,895,000 B2
(45) Date of Patent: Feb. 22, 2011

(54) ENVIRONMENTAL SENSOR, PARTICLE COUNTING SYSTEM HAVING AN ENVIRONMENTAL SENSOR, AND METHODS OF OPERATING THE SAME

(75) Inventors: David L. Chandler, Highland, CA (US); Daniel Edward Cain, Redlands, CA (US); Glenn Y. Kozuma, Twin Peaks, CA (US); Joe Somoza, Redlands, CA (US)

(73) Assignee: Venturedyne, Ltd., Pewaukee, WI (US)

( * ) Notice: Subject to any disclaimer, the term of this patent is extended or adjusted under 35 U.S.C. 154(b) by 576 days.

(21) Appl. No.: 11/849,439

(22) Filed: Sep. 4, 2007

(65) Prior Publication Data

US 2009/0063078 A1 Mar. 5, 2009

(51) Int. Cl.
*G01N 31/00* (2006.01)
(52) U.S. Cl. .................. 702/26; 340/627; 356/338; 377/50; 438/61; 702/188
(58) Field of Classification Search .............. 702/22, 702/24, 82, 188, 189, 26; 340/607, 627, 340/630; 73/23.31; 356/335, 336, 338, 339; 438/14, 61; 377/50; 250/222.1, 222.2
See application file for complete search history.

(56) References Cited

U.S. PATENT DOCUMENTS

| | | | |
|---|---|---|---|
| 3,936,741 A | 2/1976 | Coulter et al. | |
| 4,220,499 A | 9/1980 | Hughes, Jr. et al. | |
| 5,296,910 A | 3/1994 | Cole | |
| 5,467,189 A | 11/1995 | Kreikebaum et al. | |
| 5,515,164 A | 5/1996 | Kreikebaum et al. | |
| 5,523,743 A | 6/1996 | Rattman et al. | |
| 5,600,438 A | 2/1997 | Kreikebaum et al. | |
| 5,731,875 A | 3/1998 | Chandler et al. | |
| 5,767,967 A | 6/1998 | Yufa | |
| 5,825,487 A | 10/1998 | Felbinger et al. | |
| 5,870,190 A | 2/1999 | Unger | |
| 6,191,853 B1 | 2/2001 | Yamaguchi et al. | |
| RE37,353 E | 9/2001 | Kreikebaum et al. | |
| 6,346,983 B1 | 2/2002 | Yufa | |
| 6,487,523 B2 | 11/2002 | Jarman et al. | |
| 6,490,530 B1 | 12/2002 | Wyatt | |
| 6,583,404 B1 | 6/2003 | Sakurai | |
| 6,606,582 B1 | 8/2003 | Brinkman et al. | |
| 6,773,932 B2 | 8/2004 | Robinson et al. | |

(Continued)

OTHER PUBLICATIONS

International Search Report and Written Opinion of the International Searching Authority for Application No. PCT/US2008/075100 dated Nov. 14, 2008 (10 pages).

(Continued)

*Primary Examiner*—John H Le
(74) *Attorney, Agent, or Firm*—Michael Best & Friedrich LLP

(57) ABSTRACT

An environmental sensor including an inlet and an outlet such that a flow of fluid moves from the inlet to the outlet, a particle detection portion to detect particles in the fluid, and a controller connected to the particle detection portion. The environmental sensor can be in communication with a data acquisition system (e.g., via a wireless access point) to form a particle counting system. Also disclosed are methods of operating the environmental sensor and methods of operating the particle detection system.

26 Claims, 7 Drawing Sheets

U.S. PATENT DOCUMENTS

2004/0010379 A1   1/2004   Craig et al.
2004/0246479 A1   12/2004  Cartlidge et al.
2005/0151968 A1   7/2005   Drake et al.
2005/0219526 A1   10/2005  Peng
2006/0187070 A1   8/2006   Liang et al.
2006/0232773 A1   10/2006  Barton et al.
2006/0263925 A1   11/2006  Chandler
2006/0274309 A1   12/2006  Cerni et al.
2008/0148812 A1   6/2008   Wei et al.
2009/0063078 A1   3/2009   Chandler et al.

OTHER PUBLICATIONS

CI-3100 ETHERNET Optical Particle Transducer Operations Manual, Climet Instruments Company (Dec. 2006) 29 pages.

DIGI Connect ME Family Wired and Wireless Embedded Modules, Brochure 91001258 B2/705, Digi International Inc. (2004-2005) 4 pages.

United States Patent Office Action for U.S. Appl. No. 11/849,421 dated Sep. 15, 2009 (12 pages).

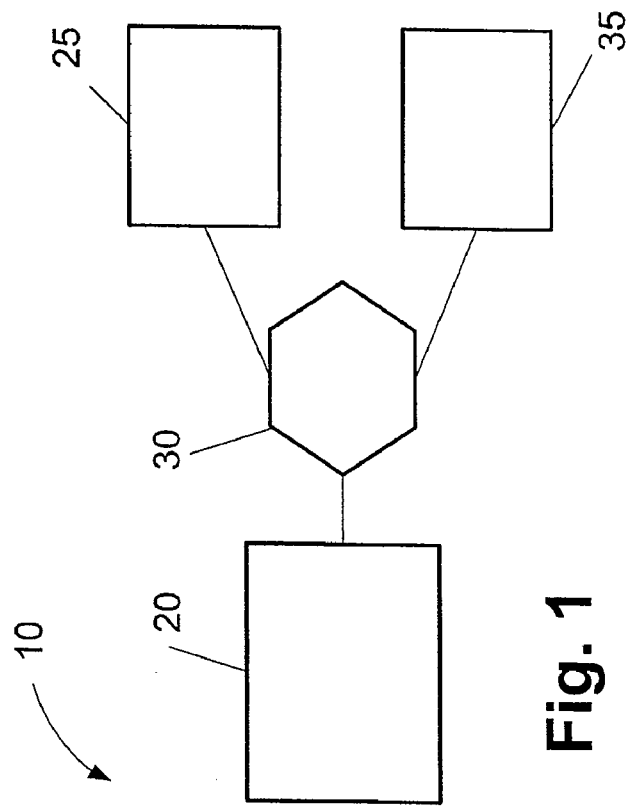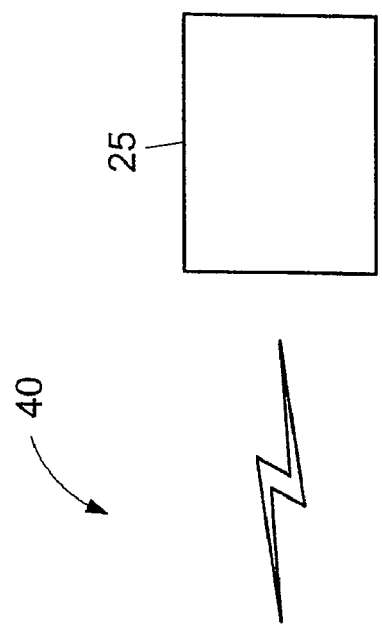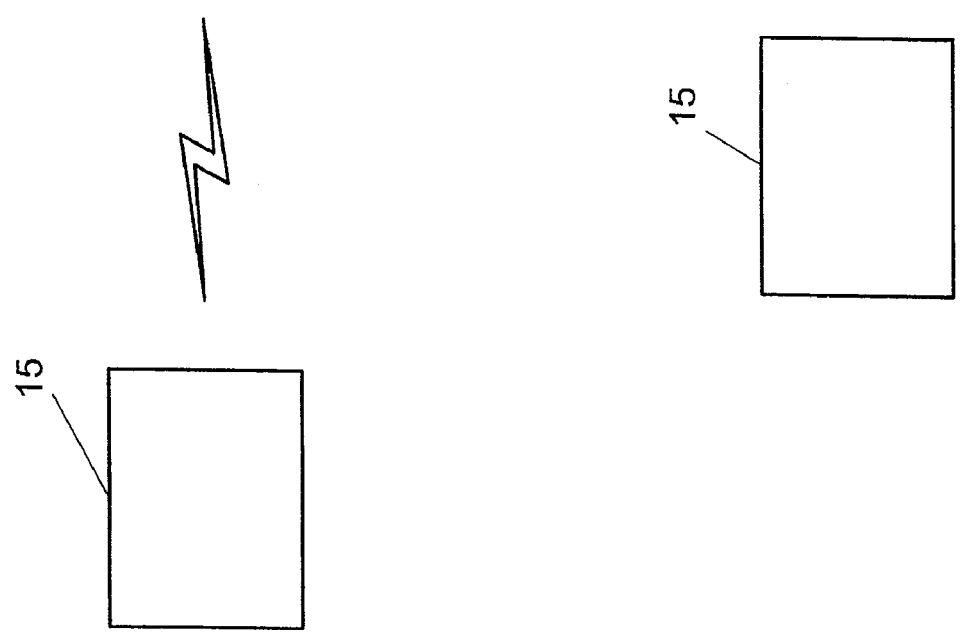

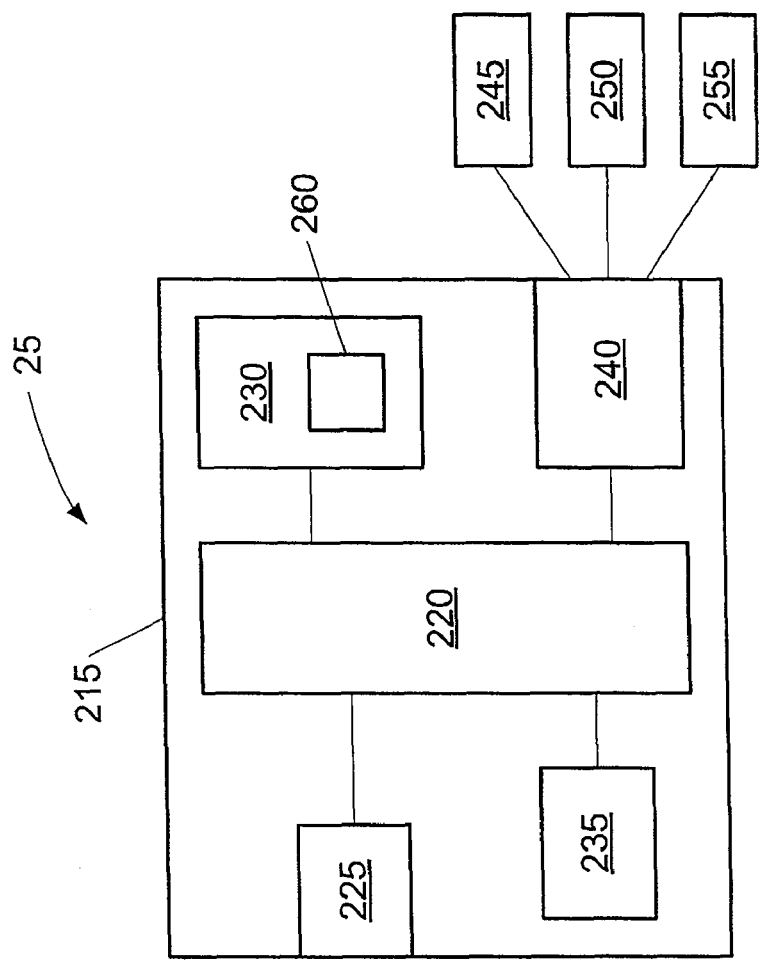
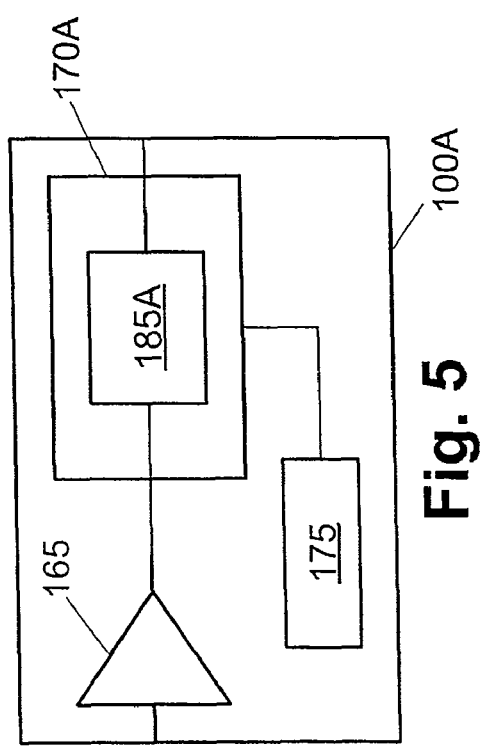
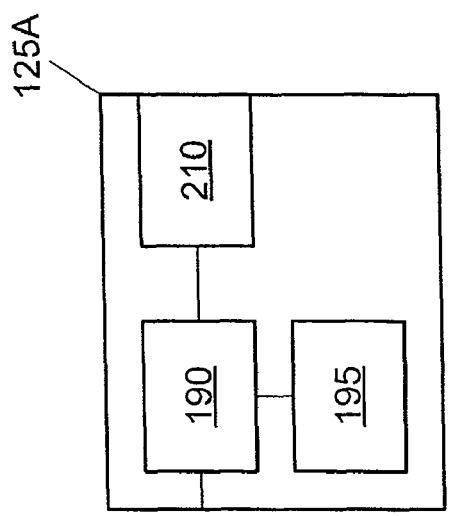
Fig. 7
Fig. 5
Fig. 6

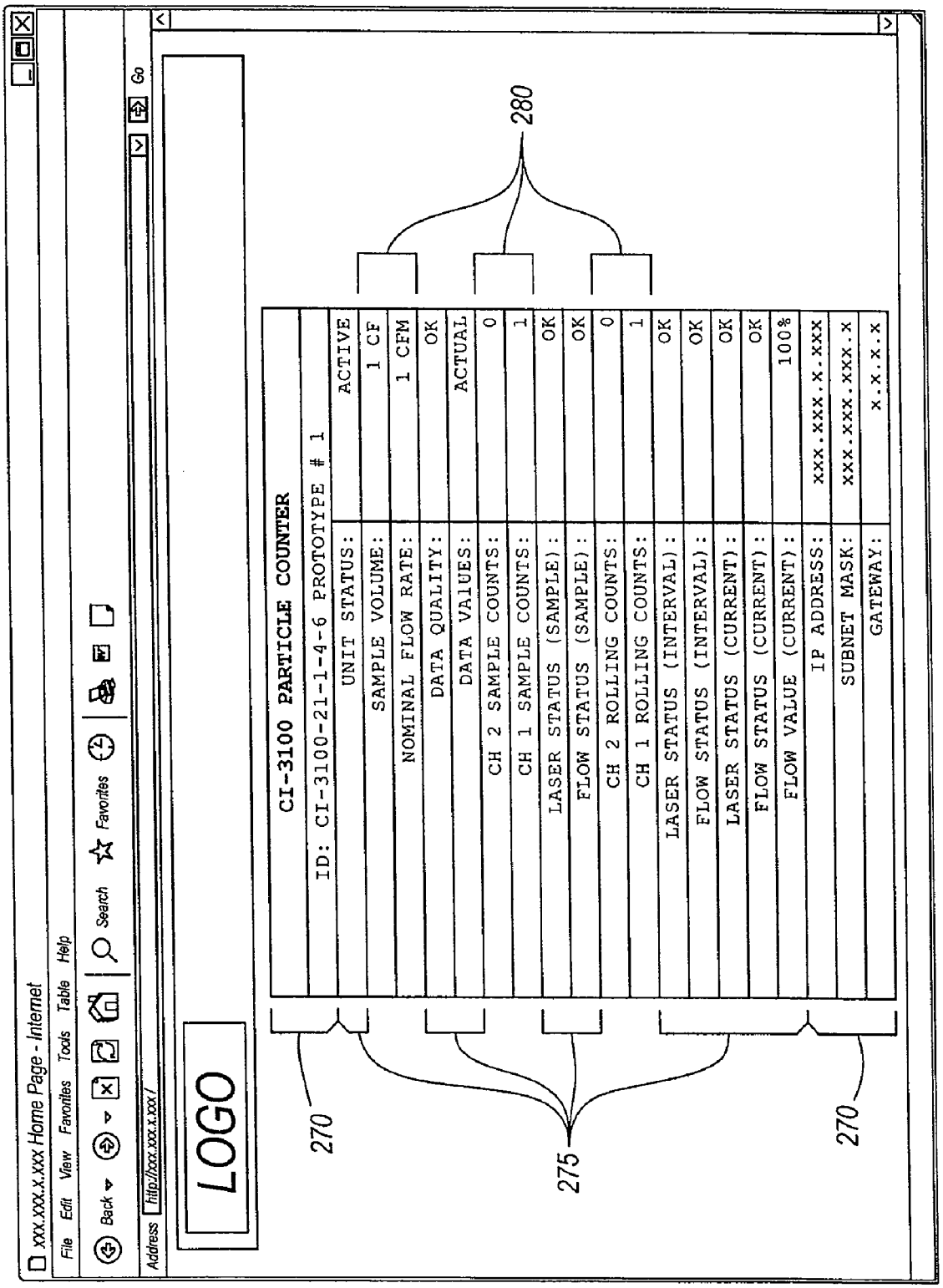

ENVIRONMENTAL SENSOR, PARTICLE COUNTING SYSTEM HAVING AN ENVIRONMENTAL SENSOR, AND METHODS OF OPERATING THE SAME

BACKGROUND

The invention relates to environmental sensors, such as particle counters that are used to detect particles in air or liquid environments. The invention also relates to particle counting systems having an environmental sensor, methods of operating the particle counting systems, and methods of operating the environmental sensor.

Particle detection, among other uses, allows for monitoring the manufacturing of a product that would be unsuitable for its intended purpose if contamination is present, even at the molecular level. For example, pharmaceutical manufacturers require environments that are sterile to avoid viable organisms from contacting a product being manufactured or packaged. Also, pharmaceutical manufacturers monitor specified areas to insure compliance with cleanliness standards.

Another industry that generally requires the use of a particle counting system in an environment is the semiconductor manufacturing industry. Semiconductor manufacturers monitor the cleanliness of their process fluids, gasses, and environments to identify and eliminate sources of contamination. Other industries can use particle counting systems to detect and control contamination that affects product performance and quality. For example, manufacturers of automotive products, portable equipment, micro-machined structures, and optical assemblies may rely on the use of particle counting systems for some of their manufacturing processes.

Accordingly, there is the need for an environmental sensor that performs, among other things, reliable particle counts and allows for access and distribution of information related to the particle counts. There is also a need for a particle counting system incorporating such an environmental sensor.

SUMMARY

In one embodiment, the invention provides a method of operating a particle counting system including an environmental sensor. The environmental sensor includes a memory having a predetermined particle count at a first memory address. The method comprises storing a detected particle count at a second memory address of the memory, receiving a first signal, copying the predetermined particle count from the first memory address to the second memory address in response to receiving the first signal, and generating a second signal based on the second memory address including the predetermined particle count.

In another embodiment, the invention provides a particle counting system. The particle counting system comprises a data acquisition system configured to generate an information request, and an environmental sensor configured to receive the information request. The environmental sensor includes an inlet and an outlet such that a flow of fluid moves from the inlet to the outlet, a particle detection portion to detect particles in the fluid, a memory including a first count at a first memory address, and a controller connected to the particle detection portion. The controller is configured to generate a second count based on the detected particles, store the second count at a second memory address of the memory, and copy the first count from the first memory address to the second memory address in response to the environmental sensor receiving the information request.

In another embodiment, the invention provides a method of operating an environmental sensor including a memory. The method comprises creating a flow of fluid through the environmental sensor, detecting particles in the fluid, determining a first particle count having a relation to the number of detected particles in a first time interval, determining a second particle count having a relation to the number of detected particles in a second time interval, determining a third particle count having a relation to the number of detected particles in a third time interval, detecting a condition of the environmental sensor during one of the first, second, and third time intervals, discarding the respective one of the first, second, and third particle counts in response to detecting the condition during one of the first, second, and third time intervals, resulting in non-discarded particle counts, and determining a total particle count based on the non-discarded particle counts.

In another embodiment, the invention provides an environmental sensor. The environmental sensor comprises an inlet and an outlet such that a flow of fluid moves from the inlet to the outlet, a particle detection portion to detect particles in the fluid during a plurality of time intervals, and a controller connected to the particle detection portion. The controller is configured to detect a condition of the environmental sensor, determine particle counts corresponding to the plurality of time intervals, and discard particle counts related to the time intervals when the condition of the environmental sensor is detected.

In another embodiment, the invention provides a particle counting system. The particle counting system includes an environmental sensor configured to receive an information request. The environmental sensor includes an inlet and an outlet such that a flow of fluid moves from the inlet to the outlet, a particle detection portion to detect particles in the fluid, and a memory including first memory address and a second memory address, the first memory address having a first count. The particle counting system also includes a controller connected to the environmental sensor over a network. The environmental sensor is configured to generate a second count based on the detected particles, and to store the second count at the second memory address. The controller is configured to send the information request to the environmental sensor to copy the first count from the first memory address to the second memory address in response to receiving the information request.

Other aspects of the invention will become apparent by consideration of the detailed description and accompanying drawings.

BRIEF DESCRIPTION OF THE DRAWINGS

FIG. 1 is a schematic representation of a particle counting system.

FIG. 2 is a schematic representation of a second particle counting system.

FIG. 5 is a schematic representation of an alternative construction for the controller illustrated in FIG. 4.

FIG. 6 is a schematic representation of an alternative construction for the communication layer illustrated in FIG. 4.

FIG. 7 is a schematic representation of a data acquisition system.

FIG. 8 is an information display in the form of a webpage.

DETAILED DESCRIPTION

Figure 3:
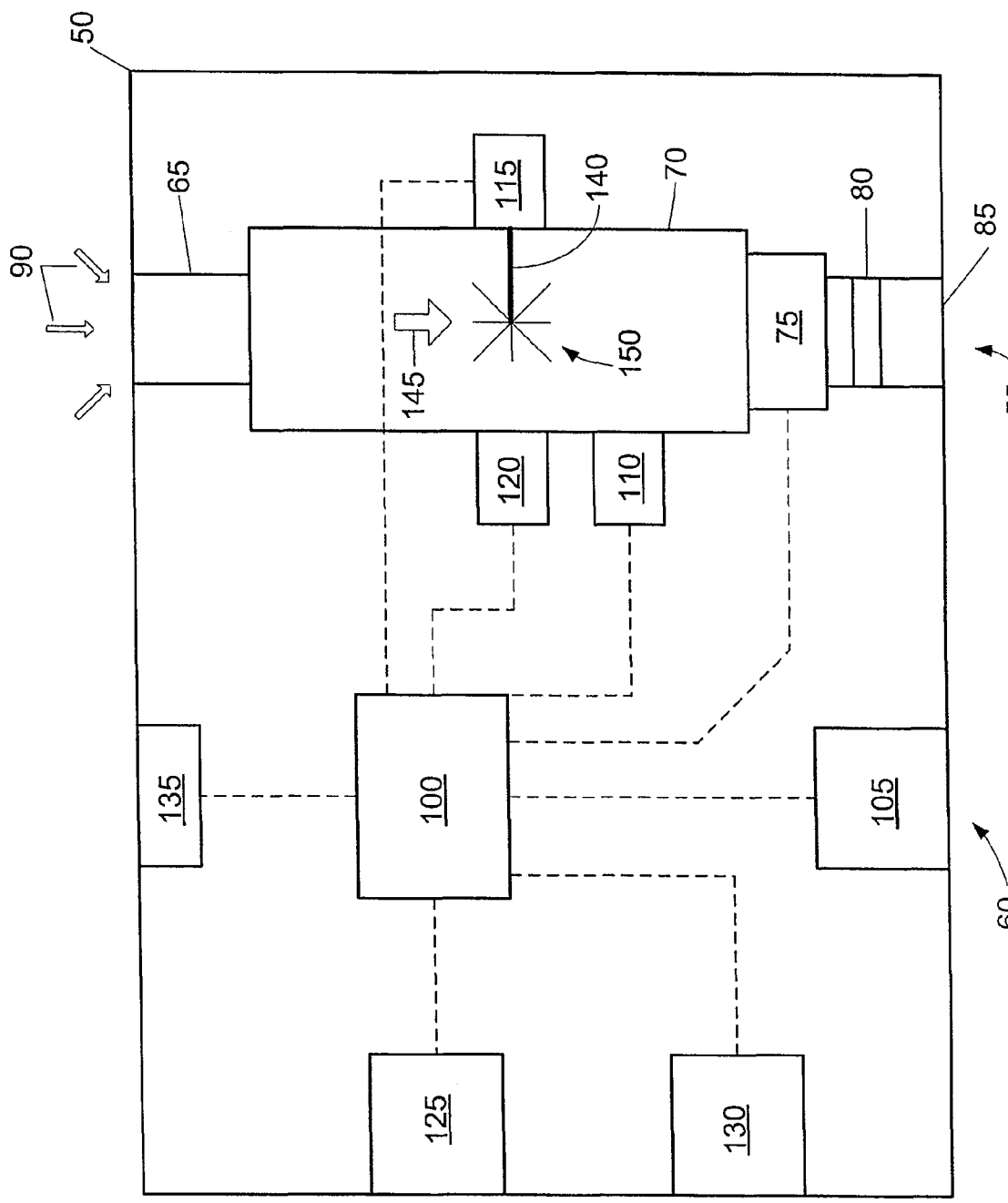
FIG. 3 is a schematic representation of a particle counter.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

Although directional references, such as upper, lower, downward, upward, rearward, bottom, front, rear, etc., may be made herein in describing the drawings, these references are made relative to the drawings (as normally viewed) for convenience. These directions are not intended to be taken literally or limit the invention in any form. In addition, terms such as "first", "second", and "third" are used herein for purposes of description and are not intended to indicate or imply relative importance or significance.

In addition, it should be understood that embodiments of the invention include hardware, software, and electronic components or modules that, for purposes of discussion, may be illustrated and described as if the majority of the components were implemented solely in hardware. However, one of ordinary skill in the art, and based on a reading of this detailed description, would recognize that, in at least one embodiment, the electronic based aspects of the invention may be implemented in software. As such, it should be noted that a plurality of hardware and software based devices, as well as a plurality of different structural components, may be utilized to implement the invention. Furthermore, and as described in subsequent paragraphs, the specific mechanical configurations illustrated in the drawings are intended to exemplify embodiments of the invention and that other alternative mechanical constructions are possible.

FIG. 1 is a schematic representation of a particle counting system 10 configured in a wireless access point topology. The particle counting system 10 includes an environmental sensor 15, a wireless access point (WAP) 20, and a data acquisition system (DAS) 25 connected to the WAP 20 via a network 30. It is envisioned that the number of environmental sensors 15, WAPs 20, etc. can vary from the construction shown.

In the illustrated construction, the environmental sensor 15 wirelessly communicates with the WAP 20 to send and receive information via wireless protocols (e.g., standard wireless protocols). The WAP 20 is connected to the network 30 via a "wired" connection. In one construction, the WAP 20 can include a NETGEAR WGR614 wireless router. The term "wired" is intended to define means of connection such as USB cable, DSL cable, Ethernet cable, and others. Similarly, the network 30 is intended to broadly cover either a connection to the Internet or also an intranet or internal network. It is also envisioned that the network 30 can include wireless connections. In addition to the specified DAS 25 shown in FIG. 1, the particle counting system 10 can also include other elements connected to the network 30, such as a computer 35.

FIG. 2 is a schematic representation of a particle counting system 40 configured with an ad-hoc topology. More specifically, the particle counting system 40 includes one or more environmental sensors 15 (only one environmental sensor 15 shown in FIG. 2) wirelessly connected to a DAS 25, which can alternatively be connected to a network 30. In constructions where the particle counting system 40 includes more than one environmental sensor 15, each environmental sensor 15 includes an address which is recognized by the DAS 25. Each environmental sensor 15 has a unique address that allows the DAS 25 to receive, store, and communicate information from the various environmental sensors 15, which may be located in distinct and remote environments. As used herein, the term "information" is broadly construed to comprise signals (e.g., analog signals, digital signals, etc.), states, data (e.g., packet data, non-packet data, etc.), etc., for providing knowledge, values, events, facts, measures, outcomes, and similar items.

With reference to FIGS. 1 and 2, the particle counting systems 10 and 40 are configured to communicate information from the environmental sensor 15 to the DAS 25 to exchange information regarding the space in which the environmental sensor 15 is located, also defined an environmental zone (e.g., a "clean" zone). One difference between the particle counting systems 10 and 40 is that, in the particle counting system 10, the DAS 25 can access the environmental sensor 15 remotely through the network 30, and in the particle counting system 40, the DAS 25 directly accesses the environmental sensor 15 through a wireless connection. It is to be understood, however, that the topologies and/or configurations described in FIGS. 1 and 2 are for exemplary purposes and that other configurations of the particle counting system may fall within aspects of the invention. For example, it is envisioned that the sensor 15 can communicate with the WAP 20 or the DAS 25 via wire means.

FIG. 3 is a schematic representation of an exemplary environmental sensor. More specifically, the environmental sensor shown in FIG. 3 is a particle counter 50 configured to detect particles within a predetermined size range. The particle counter 50 is an aerosol particle counter that operates under the principle of light scattering detection. However, other aerosol particle counters (e.g., a particle counter that operates under the principle of light obscuration) and liquid particle counters can be used, among others. The particle counter 50 includes a fluid movement portion 55 and a control portion 60. The fluid movement portion 55 includes a fluid (e.g., air) inlet 65, a particle detection portion 70, a vacuum source 75, a filter 80, and a fluid outlet 85.

In the construction shown in FIG. 3, a flow of air is created by the vacuum source 75 (e.g., an air pump or blower). The flow enters the particle counter 50 through the inlet 65, as shown by arrows 90, and traverses to the particle detection portion 70 where the portions 70 detects particles in the air, as explained in more detail below. The flow then traverses to the filter 80 and exits through the outlet 85. In FIG. 3, the vacuum source 75 is shown as being part of the flow path. However, other constructions of the particle counter 50 can include a vacuum source not directly in the path of the flow or, alternatively, the particle counter 50 can include an external vacuum source. Similarly, FIG. 3 illustrates one filter 80 located near the outlet 85. However, other constructions of the particle counter 50 can include a different number of filters (including zero) and the location of the filter may vary. In yet other constructions, the fluid movement portion 75 can include a tube or hose with one end connected to the inlet 65 such that the vacuum source (internal or external) generates a flow from the other end of the tube and through the particle counter 50 as explained above.

The control portion 60 of the particle counter 50 includes a controller 100 operable to control and operate the particle counter 50. The control portion 60 also includes a power source 105, a flow sensor 110, a light source 115 (e.g., a laser beam generator), an optical detector 120, a communication layer 125, a display system 130, and an I/O layer 135. During operation of the particle counter 50, the flow sensor 110 is operable to generate a signal indicative of the mass of the air flowing through the particle counter 50. The signal generated by the flow sensor 110 allows the controller 100 to operate the vacuum source 75 to maintain a constant flow through the particle counter 50. For example, the controller 100 can operate the vacuum source 75 to maintain a constant flow rate of 1 cubic foot per minute ($ft^3$/m in), which is substantially equal to 28.3 liters per minute (lt/min). However, the vacuum source 75 can generate other flow rates based on desired parameters or the particular application of the particle counter 50. In other constructions, the environmental sensor 50 can include an external vacuum source not connected to the control portion 60 such that the external vacuum source is controlled independently with respect to the control portion to generate a fluid flow through the particle counter 50.

Still with reference to FIG. 3, the display system 130 includes a multiple light display to indicate the status of the particle counter 50. More particularly, the display system 130 includes an "on/off" type display related to the power source, an alarm system, a particle count interval, the light source, and the flow status. For example, the display system 130 can indicate whether the particle counter is on or off, whether a fault related to the air flow or light source 115 is detected, whether the counter 50 is detecting a particle, whether the light source 115 is operating, and whether the flow rate remains constant. Other constructions of the particle counter 50 can include the display system 130 with a different number and combination of lights, or alternatively a different display element (e.g., an LCD screen). Though not particularly described, the I/O layer 135 illustrates alternative input/output connections, displays, and/or switches allowing a user to control and/or interact with the particle counter 50.

During operation of the particle counter 50, particles are detected by light scattering. More specifically, the light source 115 generates a laser beam 140 within the particle detection portion 70 of the particle counter 50. Particles flow through the particle detection portion 70, as shown by arrow 145, and through the laser beam 140. The particles traversing the particle detection portion 70 result in light scattering (represented by 150), which is detected by the optical detector 120. The optical detector 120 generates a voltage pulse as a result of detecting the light scattering 150 and sends the voltage pulse to the controller 100. The controller 100 is operable to determine information regarding the particles (e.g., particle size, velocity, composition) based on the voltage pulse generated by the optical detector 120. The information determined by the controller 100 can be saved in memory and/or sent to the DAS 25, for example, by the communication layer 125 of the particle counter 50.

Figure 4:
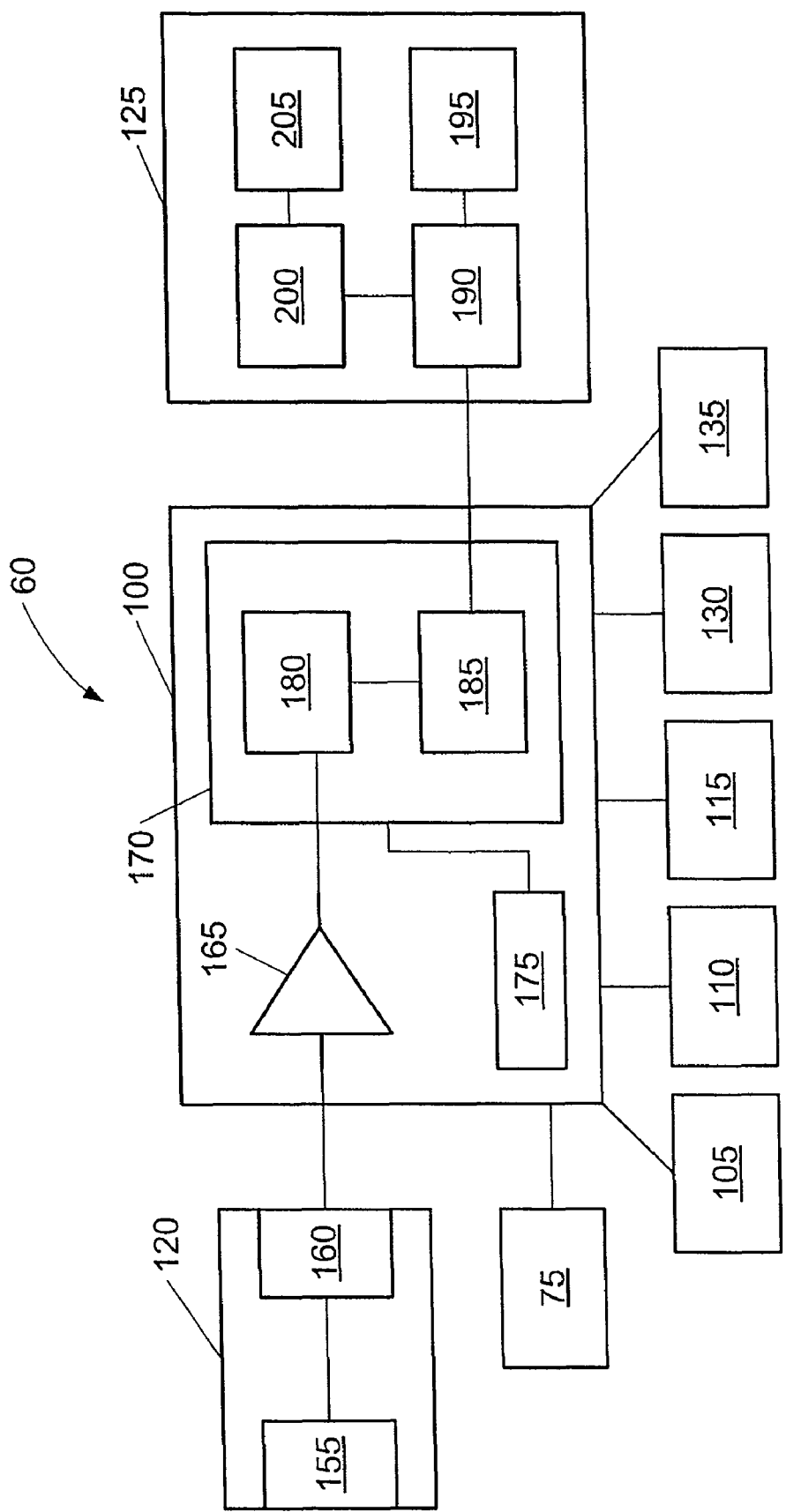
FIG. 4 is a partial schematic representation of the particle counter illustrated in FIG. 3.

FIG. 4 is a schematic representation of the control portion 60 as it relates more specifically to the detection of particles, and to the processing and transmitting of information related to the detected particles. Accordingly, FIG. 4 illustrates in more detail the optical detector 120, the controller 100, and the communication layer 125. The vacuum source 75, power source 105, flow sensor 110, light source 115, display system 130, and I/O layer 135 are also shown connected to the controller 100 for illustration purposes. The optical detector 120 includes a photo detector and optics 155 to detect the scattering light 150, and an amplifier 160 to generate a voltage pulse as a result of detecting the scattering 150. The controller 100 includes additional amplifiers 165, a processor 170, and a memory 175. The processor 170 includes an analog-to-digital converter (A/D) 180 and a pulse height analyzer or voltage comparator 185. The processor 170 may take the form of a microprocessor, a digital signal processor, a microcontroller, or similar devices that can execute instructions. Of course, the A/D converter 180 and/or voltage comparator 185 can be distinct from the processor 170, and the memory 175 can be combined with the processor 170.

The voltage pulse generated by the optical detector 120 is received for processing at the controller 100 by the amplifier(s) 165 and the processor 170. More specifically, the amplifier(s) 165 can amplify and filter the voltage pulse, and the A/D 180 can transform the voltage pulse into a digital signal for the voltage comparator 185 to analyze. The voltage comparator 185 analyzes the digital signal by comparing the signal to predetermined values or voltage thresholds. Based on the comparison, the processor 170 can determine whether the voltage pulse was greater than a voltage threshold, for example, and save the information in the memory 175. As the controller 100 receives pulses generated by the optical detector 120, a count of particles with predetermined characteristics (e.g., particle size) can be stored in the memory 175.

FIG. 5 is a schematic representation of a controller 100A, which is an alternative construction of the controller 100 shown in FIG. 4. The controller 100A includes the amplifier(s) 165 and the memory 175. The controller 100A also includes a processor 170A with a voltage comparator 185A that compares analog voltage pulses generated by the optical detector 120 (not shown in FIG. 5). Accordingly, the controller 100A analyses and determines particle size information based on analog signals, whereas the controller 100 analyzes and determines particle size information based on digital signals.

In one exemplary construction of the particle counter 50, two particle counts are stored in the memory 175. The first particle count is a count of particles with a size greater than 0.5 microns. The second particle count is a count of particles with a size greater than 5 microns. In other constructions, a different particle counts can be stored in the memory 175. The voltage thresholds related to each particle size (e.g., 0.5 microns and 5 microns) are determined through a calibration process of the particle counter 50. The calibration process can include creating an aerosol cloud of particles with a known size, such as 0.5 microns or 5 microns, and allowing the aerosol cloud to flow through particle counter 50. The DAS 25 can be used in the calibration process to observe the particle size detected by the particle counter 50 such that an operator can adjust the particle counter 50 until the correct information is generated. Though the particle counter 50 can be calibrated to detect a wide range of particle sizes, the particle counter 50 is usually calibrated to sense particles with a size of 0.5 microns and 5 microns because 0.5 microns relates to a specific cleanliness level for a clean zone, and 5 microns relates to the size of bacteria or similar elements that are of interest for a clean zone.

Referring again to FIG. 4, the communication layer 125 includes a processor 190, a memory 195, a modulator/demodulator circuit 200, and an antenna 205. In one exemplary construction of the particle counter 50, the communication layer 125 includes a Digi Connect wireless module to allow communication between the particle counter 50 and a second device. More specifically, the communication layer 125 receives the particle size information from the controller 100 and is operable to wirelessly transmit the information to the WAP 20, as shown in FIG. 1, or directly to the DAS 25 in an ad-hoc topology, as shown in FIG. 2. In some constructions, the communication layer 125 can include a web page design stored in the memory 195, be operable to combine particle count information and/or status information (of the particle counter 50) with the web page design, and transmit the combined information. The communication layer 125 also receives information and/or instructions to operate the particle counter 50. For example, the communication layer 125 can receive particle count requests from the DAS 25 or a status request from a computer (e.g., computer 35 shown in FIG. 1).

FIG. 6 is a schematic representation of a communication layer 125A, which is an alternative construction of the communication layer 125 shown in FIG. 4. The communication layer 125A includes the processor 190 and the memory 195. The communication layer 125A also includes a wire connector, such as an RJ-45 connector 210, for communication with another device or network. In yet another construction, the particle counter 50 can include a communication layer that is integrally manufactured with a controller. The controller would then be operable to control and communicate as described in regards to the controller 100 and the communication layers 125 or 125A.

FIG. 7 is a schematic representation of the DAS 25 shown in FIGS. 1 and 2. In the illustrated construction, the DAS 25 includes a computer system 215 having a processor 220, a communication layer 225, a memory 230, a display system 235, and an I/O layer 240. The computer system 215 is described herein as it relates to the particle counter 50. However, the computer system 215 can communicate with other devices, such as the sensing devices illustrated in FIG. 7. The sensing devices can include a temperature sensor 245, a humidity sensor 250, and a pressure sensor 255.

With reference to FIGS. 1, 2 and 7, the DAS 25 is configured to communicate with the environmental sensor 15 to send information, such as control commands or data requests, and to receive information, such as particle counts and status of the environmental sensor 15. In the illustrated construction, the DAS 25 includes a set of instructions identified as a driver 260 that are designed specifically to operate the environmental sensor 15. For example, the driver 260 can take data collected by the particle counter 50, and alternatively take data from other sensors such as the temperature sensor 245, humidity sensor 250, and pressure sensor 255, and send the data to a database for storage. The driver 260 can also transfer the data to a memory location where it can be retrieved for further processing. Processing of the data by the DAS 25 can include comparing the data to predetermined thresholds and to present the data through the display system 235 in a manner that is significant to the user. The driver 260 can also include instructions to operate specific elements of the particle counter 50. For example, the driver 260 can individually operate and monitor the vacuum source 75, light source 115, and display system 130.

In the constructions shown in FIGS. 1 and 2, the particle counting system 10, 40 can include the particle counter 50 calibrated to detect particles with a size larger than 0.5 microns. Further, the computer system 215 with the driver 260 can be configured to move data related to particle counts to specific memory addresses in the particle counter 50, to retrieve data related to particle counts combined with web page information from the communication layer 125, and to display the retrieved data with the display system 235. FIG. 8 is an exemplary information display 265 generated by the display system 235. The information display 265 displays various information, which may include system information 270, status information 275, and count information 280. The information display 265 is illustrated in the form of a webpage accessed by the computer system 215 though the network 30, for example. Because the communication layer 125 of the particle counter 50 can include web page design information, the display 265 can take the form of the webpage shown in FIG. 8 when the particle counter 50 and computer system 215 are in an ad-hoc topography, as shown in FIG. 2. The system information 270 refers to the specific type of particle counter 50 and network connection. The status information 275 refers to the status of the particle counter 50 as well as the status of specific elements of the particle counter 50, such as the light source 115 and vacuum source 75. The count information 280 refers to data detected by the particle counter 50, such as flow rate and particle counts.

Figure 9:
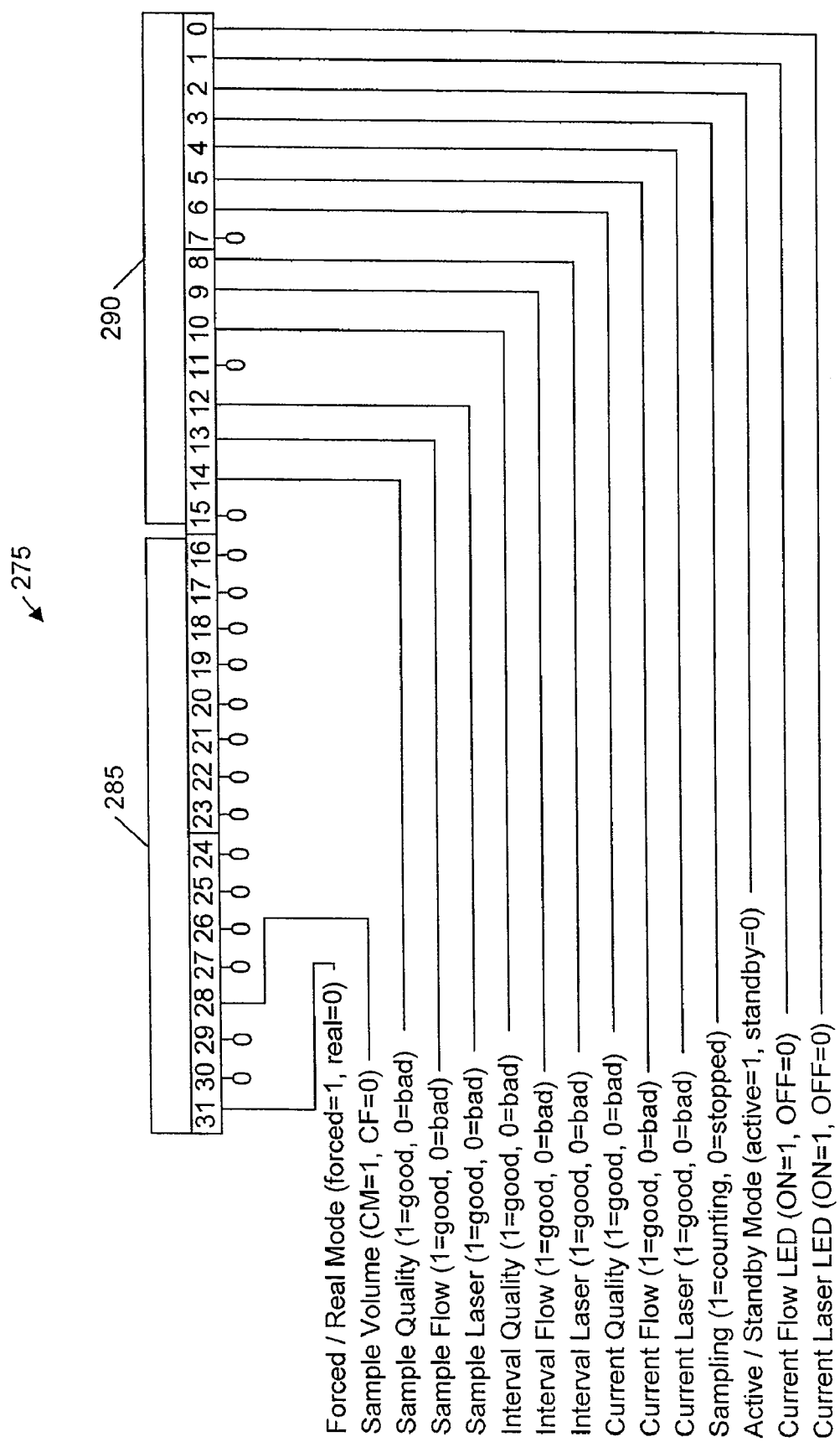
FIG. 9 is a schematic representation of a status register.
Figure 10:
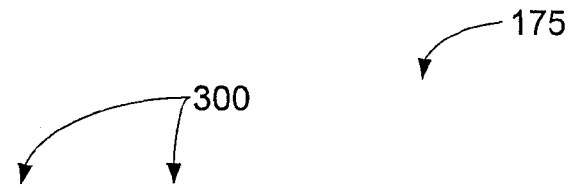
FIG. 10 is a table illustrating a plurality of memory addresses.

FIG. 9 is a schematic representation of the status information 275 stored in a memory location of the memory 175. More specifically, the status information 275 is shown in a first memory address 285 and a second memory address 290, each address being a 16-bit memory address. For the computer system 215 to display the status information 275, the driver 260 needs only to retrieve information in memory addresses 285, 290. The computer system 215 matches specific bits of the memory addresses 285, 290 to the status of a corresponding element of the particle counter 50, and displays the status information 275 (e.g., light source being on or off) accordingly. FIG. 10 is a schematic representation of the memory 175 including a number of memory addresses 300 dedicated to different types of counts and information related to the particle counter 50 (e.g., status information). With specific reference to the count information 280, the driver 260 retrieves the count information 280 from specific memory addresses (e.g., memory addresses 12 and 13) in the memory 175 of the particle counter 50. The computer system 215 is operable to display the count information 280 (e.g., the number of particles with particle size larger than 0.5 microns) as a result of retrieving the count from a dedicated memory address in memory 175. Therefore, size information of the particle is not sent or generated by the particle counter 50. The display system 235 can display size information with the count information 280 based on the known calibration of the particle counter 50 and the dedicated address in the memory 175 where the count information 280 was retrieved. Similarly, status information 275 can be retrieved from a specific address in the memory 175 of the particle counter 50. As a result, data transfer between the particle counter 50 and the computer system 215 is improved.

With specific reference to the operation of the particle counter 50, the particle counter 50 is calibrated to establish, among other parameters, the size of the particles to be detected and the flow rate. As indicated above, the particle counter 50 can be calibrated to detect particles of two particle sizes (e.g., particle size larger than 0.5 microns and particle size larger than 5 microns). The particle counter 50 is also calibrated to have a substantially constant flow rate. For example, the particle counter 50 can be calibrated to generate a flow rate of about 1 ft$^3$/min (about 28.3 lt/min). In other constructions, the particle counter 50 can be calibrated to generate different flow rates, such as 25 lt/min, 50 lt/min, 75 lt/min, and 100 lt/min. Based on the calibrated flow rate, it is possible to determine the amount of time it takes for the particle counter 50 to sample the complete volume of a clean zone. For analysis purposes, predetermined sample volumes are established such that a particle count can be displayed as a function of a standard unit of volume (e.g., 1 m$^3$ or 1 ft$^3$. Accordingly, for a particle counter 50 calibrated to generate a flow rate of 1 ft$^3$/min, it is determined that the particle counter 50 can sample a sample volume of 1 m$^3$ in about 35.3 minutes, and a sample volume of 1 ft$^3$ in about 1 minute.

In the illustrated construction, the particle counter 50 is further configured to sample a sample volume in intervals.

More specifically, the particle counter 50 is configured to sample a sample volume in sixty intervals. Accordingly, if the sample volume is established to be 1 m$^3$, the particle counter 50 can sample $\frac{1}{60}$ m$^3$ in about 35.3/60 minutes. Similarly, if the sample volume is established to be 1 ft$^3$, the particle counter 50 can sample $\frac{1}{60}$ ft$^3$ in about one second. Based on the application and/or desired characteristics of the particle counter 50, other constructions can include the particle counter 50 being calibrated to sample full sample volumes with a different number of intervals. Sampling the sample volume using time intervals allows the particle counter 50 to store information related to partial counts in the memory 175. For example, the memory 175 can include dedicated memory addresses (e.g., memory addresses 300) for partial count information, such as the number of particles for one time interval or the total particle count retrievable by the DAS 25 before the full sample volume has been sampled or the particle count for a previously completed sample. In addition, sampling the sample volume using intervals allows the particle counter 50 to include operational features, defined as rolling counts, forced counts, and fault detection/salvaging data.

Rolling Counts

The rolling counts feature allows the particle counter 50 to determine and store a particle count for the most recent sample volume. More specifically, the rolling counts feature is implemented by the particle counter 50 continuously adding the particle counts of time intervals. As indicated above, once sixty time intervals have elapsed, the particle count of the full sample volume is available at a predetermined memory address 300. As the particle counter 50 continues to sample the clean zone, the particle counter 50 uses the particle count taken during the latest interval and discards the particle count taken from the oldest interval to update the particle count of the full sample volume. Consequently, the particle count saved in the memory address corresponding to the particle count of the full sample volume is the count obtained during the most recent sample volume. In the illustrated construction, memory addresses 300 identified as 0 and 1 in FIG. 10 correspond to the particle count of the full sample volume for particles larger than 0.5 microns. Similarly, memory addresses 300 identified as 2 and 3 in FIG. 10 correspond to the particle count of the full sample volume for particles larger than 5 microns.

Forced Counts

The forced counts feature allows the DAS 25 to utilize the particle counter 50 to test the operation of the programming logic of the DAS under fault conditions. The forced counts feature also tests an alarm system (not shown) that actuates as a result of a fault condition, or as a result of comparing the particle counts obtained from the particle counter 50 to predetermined threshold values. As shown in FIG. 10, memory addresses 300 defined by numerals 26 through 51 correspond to forced count information saved in the memory 175. More specifically, the driver 260 of the DAS 25 includes instructions to command the particle counter to take information from addresses 300 dedicated to forced count information and copy (also sometimes referred to as move) the information to corresponding memory addresses 300 where actual or detected information is saved during operation of the particle counter 50. The driver 260 then reads the information from the memory 175 as if the DAS 25 is retrieving actual detected information. In one example, if a user tests for actuation of an alarm when the particle count of a sample volume is larger than a predetermined threshold, the driver 260 commands the particle counter to take the count from memory addresses 300 corresponding to forced count information, and copy the information to the memory addresses 300 where the particle count is saved during operation of the particle counter 50, and retrieves the information to the DAS 25. The test is considered successful when the alarm is activated as a result of the DAS 25 receiving and processing the forced count information. As shown in FIG. 10, every memory address 300 that includes forced count information has a corresponding memory address 300 that includes information stored during operation of the particle counter 50.

Alternatively, an auxiliary computer or controller (e.g., computer 35 of the particle counting system 10 illustrated in FIG. 1) other than the DAS may be equipped with a program operable to control the particle counter and communicate with the particle counter over the network. In this scenario, the auxiliary computer sends commands to cause the particle counter to send forced counts and status information to the DAS under test. The DAS programming is tested in this scenario without the necessary test programs being run in the DAS itself.

Fault Detection/Data Salvaging

The fault detection feature allows the particle counter 50 to provide accurate, as well as timely count information. More specifically, the particle counter 50 can detect a fault condition and can react to the fault condition such that the particle count information is uncorrupted. The particle counter 50 can detect fault conditions such as malfunction of the light source 115 or air flow interruption, for example. In the case of a fault condition, the memory address corresponding to status information 275, as shown in FIG. 9, are updated. Consequently, the particle counter 50 discards the count information obtained in the interval during which the fault condition occurred. Once the status information 275 indicates the fault condition does not exist, the particle counter 50 updates the total particle count with the counts detected in the interval during which the fault condition is no longer detected. This procedure allows the particle counter 50 to provide count information for a full sample volume without having to discard all the counts corresponding to that sample volume in the situation where a fault condition is detected. For example, if the sample volume is determined to be 1 ft$^3$ and a fault condition was detected during one of the sixty intervals, the particle counter 50 can provide with a particle count of the full sample volume in about 61 seconds (one additional second than the case in which no fault condition is detected). Accordingly, the count detected during one faulty interval is discarded instead of discarding the particle count determined for the whole sample volume.

Various features and advantages of the invention are set forth in the following claims.

What is claimed is:

1. A particle counting system comprising:
    a data acquisition system configured to generate an information request; and
    an environmental sensor configured to receive the information request, the environmental sensor including
        an inlet and an outlet such that a flow of fluid moves from the inlet to the outlet,
        a vacuum source operable to create the flow of fluid between the inlet and the outlet,
        a particle detection portion to detect particles in the fluid,
        a memory including a first count at a first memory address, and
        a controller connected to the particle detection portion, the controller being configured to generate a second count based on the detected particles, store the second count at a second memory address of the memory, and copy the first count from the first memory address to the second memory address in response to the environmental sensor receiving the information request.

2. The particle counting system of claim 1, wherein the vacuum source is in a space within the environmental sensor and is connected to the controller.

3. The particle counting system of claim 1, wherein the environmental sensor further includes a communication layer operable to receive the information request and to generate a signal based on the first count in the second memory address.

4. The particle counting system of claim 3, wherein the communication layer includes an antenna to wirelessly receive a signal including the information request and send the signal based on the first count.

5. The particle counting system of claim 4, wherein the communication layer includes display information, and wherein the communication layer is configured to combine and wirelessly transmit the display information with the signal based on the first count.

6. The particle counting system of claim 3, wherein the data acquisition system includes an alarm configured to generate a warning in response to the data acquisition system receiving the signal based on the first count.

7. The particle counting system of claim 1, further comprising a wireless access point, the environmental sensor wirelessly communicating the first count in the second memory address to the data acquisition system via the wireless access point.

8. A particle counting system comprising:
an environmental sensor configured to receive an information request, the environmental sensor including
an inlet and an outlet such that a flow of fluid moves from the inlet to the outlet,
a particle detection portion to detect particles in the fluid, and
a memory including a first memory address and a second memory address, the first memory address having a first count;
a vacuum source operable to create the flow of fluid between the inlet and the outlet; and
a controller connected to the environmental sensor over a network, the environmental sensor being configured to generate a second count based on the detected particles, and to store the second count at the second memory address, and the controller being configured to send the information request to the environmental sensor to copy the first count from the first memory address to the second memory address in response to receiving the information request.

9. The particle counting system of claim 8, wherein the vacuum source is in a space within the environmental sensor and is operated by the controller.

10. The particle counting system of claim 8, wherein the environmental sensor further includes a communication layer operable to receive the information request and to generate a signal based on the first count in the second memory address.

11. The particle counting system of claim 10, wherein the communication layer includes an antenna to wirelessly receive a signal including the information request and send the signal based on the first count.

12. The particle counting system of claim 11, wherein the communication layer includes display information, and wherein the communication layer is configured to combine and wirelessly transmit the display information with the signal based on the first count.

13. The particle counting system of claim 10, further comprising an alarm configured to generate a warning in response to the controller receiving the signal based on the first count.

14. The particle counting system of claim 8, further comprising a wireless access point to connect the environmental sensor to the network, the environmental sensor wirelessly communicating the first count in the second memory address to the controller via the wireless access point.

15. A particle counting system comprising:
a data acquisition system configured to generate an information request; and
an environmental sensor configured to receive the information request, the environmental sensor including
an inlet and an outlet such that a flow of fluid moves from the inlet to the outlet,
a particle detection portion to detect particles in the fluid,
a memory including a first count at a first memory address,
a controller connected to the particle detection portion, the controller being configured to generate a second count based on the detected particles, store the second count at a second memory address of the memory, and copy the first count from the first memory address to the second memory address in response to the environmental sensor receiving the information request, and
a communication layer operable to receive the information request and to generate a signal based on the first count in the second memory address.

16. The particle counting system of claim 15, wherein the vacuum source is in a space within the environmental sensor and is connected to the controller.

17. The particle counting system of claim 15, wherein the communication layer includes an antenna to wirelessly receive a signal including the information request and send the signal based on the first count.

18. The particle counting system of claim 17, wherein the communication layer includes display information, and wherein the communication layer is configured to combine and wirelessly transmit the display information with the signal based on the first count.

19. The particle counting system of claim 15, wherein the data acquisition system includes an alarm configured to generate a warning in response to the data acquisition system receiving the signal based on the first count.

20. The particle counting system of claim 15, further comprising a wireless access point, the environmental sensor wirelessly communicating the first count in the second memory address to the data acquisition system via the wireless access point.

21. A particle counting system comprising:
an environmental sensor configured to receive an information request, the environmental sensor including
an inlet and an outlet such that a flow of fluid moves from the inlet to the outlet,
a particle detection portion to detect particles in the fluid, and
a memory including a first memory address and a second memory address, the first memory address having a first count;
a controller connected to the environmental sensor over a network, the environmental sensor being configured to generate a second count based on the detected particles, and to store the second count at the second memory address, and the controller being configured to send the information request to the environmental sensor to copy the first count from the first memory address to the second memory address in response to receiving the information request; and wherein the environmental sensor further includes a communication layer operable to receive the information request and to generate a signal based on the first count in the second memory address.

22. The particle counting system of claim 21, wherein the vacuum source is in a space within the environmental sensor and is operated by the controller.

23. The particle counting system of claim 21, wherein the communication layer includes an antenna to wirelessly receive a signal including the information request and send the signal based on the first count.

24. The particle counting system of claim 23, wherein the communication layer includes display information, and wherein the communication layer is configured to combine and wirelessly transmit the display information with the signal based on the first count.

25. The particle counting system of claim 21, further comprising an alarm configured to generate a warning in response to the controller receiving the signal based on the first count.

26. The particle counting system of claim 21, further comprising a wireless access point to connect the environmental sensor to the network, the environmental sensor wirelessly communicating the first count in the second memory address to the controller via the wireless access point.

* * * * *